(12) United States Patent
Sungarian et al.

(10) Patent No.: US 9,233,007 B2
(45) Date of Patent: Jan. 12, 2016

(54) EXPANDABLE SELF-ANCHORING INTERBODY CAGE FOR ORTHOPEDIC APPLICATIONS

(71) Applicants: Arno Sungarian, Shrewsbury, MA (US); Philip Kuszpa, Shrewsbury, CA (US); W. Riley Allen, Apopka, FL (US); Bradley Cole, Winter Springs, FL (US)

(72) Inventors: Arno Sungarian, Shrewsbury, MA (US); Philip Kuszpa, Shrewsbury, CA (US); W. Riley Allen, Apopka, FL (US); Bradley Cole, Winter Springs, FL (US)

(73) Assignee: Blue Tip Biologics, LLC, Orlando, FL (US)

( * ) Notice: Subject to any disclaimer, the term of this patent is extended or adjusted under 35 U.S.C. 154(b) by 160 days.

(21) Appl. No.: 13/766,562

(22) Filed: Feb. 13, 2013

(65) Prior Publication Data

US 2013/0158669 A1    Jun. 20, 2013

Related U.S. Application Data

(60) Provisional application No. 61/597,865, filed on Feb. 13, 2012.

(51) Int. Cl.
*A61F 2/44* (2006.01)
*A61F 2/28* (2006.01)
*A61F 2/30* (2006.01)

(52) U.S. Cl.
CPC .............. *A61F 2/442* (2013.01); *A61F 2/447* (2013.01); *A61F 2002/2835* (2013.01); *A61F 2002/30507* (2013.01); *A61F 2002/30556* (2013.01); *A61F 2002/30772* (2013.01)

(58) Field of Classification Search
CPC ......... A61F 2/44; A61F 2/442; A61F 2/4455; A61F 2/447; A61F 2002/30556; A61F 2002/4475

USPC ............................................ 623/17.11–17.16
See application file for complete search history.

(56) References Cited

U.S. PATENT DOCUMENTS

| | | | | |
|---|---|---|---|---|
| 4,863,476 | A * | 9/1989 | Shepperd | 623/17.15 |
| 6,419,705 | B1 * | 7/2002 | Erickson | 623/17.16 |
| 6,447,544 | B1 | 9/2002 | Michelson | |
| 6,454,806 | B1 * | 9/2002 | Cohen et al. | 623/17.15 |
| 6,641,614 | B1 * | 11/2003 | Wagner et al. | 623/17.15 |
| 6,706,070 | B1 * | 3/2004 | Wagner et al. | 623/17.15 |
| 6,863,673 | B2 * | 3/2005 | Gerbec et al. | 606/99 |
| 7,094,257 | B2 * | 8/2006 | Mujwid et al. | 623/17.15 |
| 7,217,291 | B2 * | 5/2007 | Zucherman et al. | 623/17.15 |

(Continued)

*Primary Examiner* — Christian Sevilla
*Assistant Examiner* — Eric S Gibson
(74) *Attorney, Agent, or Firm* — Watson LLP; Coleman W. Watson

(57) ABSTRACT

The present invention is directed to an expandable spinal fusion intervertebral implant and a method for surgically implanting said implant that provides for maintaining and creating lordosis in the human spine that can be filled with biologics while in situ to encourage spinal fusion. A threaded rod that traverses an insertion/injection handle can be rotated to operate a screw within the interbody cage that displaces opposing vertical tapped sliding wedges, causing them to converge towards each other. Such contact causes the operation of a horizontal wedge that acts as a lift to expand the interbody cage to one of various dimensions in a preferred range. In its expanded height, the overall length of the interbody cage is maintained. At its desired expansion, the spinal fusion implant of the present invention is sized to fit within the disc space between two vertebral bodies and fill all voids left while the vertical and horizontal wedges operate within, due to the biologics being contained within the interbody cage.

21 Claims, 26 Drawing Sheets

(56) References Cited

U.S. PATENT DOCUMENTS

| | | | |
|---|---|---|---|
| 7,727,279 B2* | 6/2010 | Zipnick et al. | 623/17.11 |
| 7,837,734 B2* | 11/2010 | Zucherman | A61F 2/4425 |
| | | | 623/17.15 |
| 7,883,542 B2* | 2/2011 | Zipnick | 623/17.11 |
| 8,105,382 B2 | 1/2012 | Olmos | |
| 8,187,332 B2* | 5/2012 | McLuen | A61F 2/4455 |
| | | | 623/17.16 |
| 8,366,777 B2* | 2/2013 | Matthis et al. | 623/17.16 |
| 8,491,659 B2* | 7/2013 | Weiman | 623/17.16 |
| 8,518,120 B2* | 8/2013 | Glerum et al. | 623/17.16 |
| 8,568,481 B2* | 10/2013 | Olmos et al. | 623/17.15 |
| 8,591,585 B2* | 11/2013 | McLaughlin et al. | 623/17.15 |
| 8,591,587 B2* | 11/2013 | Refai et al. | 623/17.15 |
| 8,603,170 B2* | 12/2013 | Cipoletti et al. | 623/17.15 |
| 8,636,746 B2* | 1/2014 | Jimenez et al. | 606/99 |
| 8,663,329 B2* | 3/2014 | Ernst | 623/17.15 |
| 8,845,734 B2* | 9/2014 | Weiman | 623/17.16 |
| 8,852,279 B2* | 10/2014 | Weiman | 623/17.11 |
| 2008/0140207 A1* | 6/2008 | Olmos et al. | 623/17.16 |
| 2010/0204795 A1* | 8/2010 | Greenhalgh | 623/17.16 |
| 2010/0211176 A1* | 8/2010 | Greenhalgh | 623/17.15 |
| 2010/0292796 A1* | 11/2010 | Greenhalgh et al. | 623/17.11 |
| 2012/0035729 A1* | 2/2012 | Glerum et al. | 623/17.15 |
| 2013/0158669 A1* | 6/2013 | Sungarian et al. | 623/17.16 |
| 2013/0190876 A1* | 7/2013 | Drochner et al. | 623/17.16 |
| 2013/0211526 A1* | 8/2013 | Alheidt et al. | 623/17.16 |
| 2013/0231747 A1* | 9/2013 | Olmos et al. | 623/17.16 |

* cited by examiner

EXPANDABLE SELF-ANCHORING INTERBODY CAGE FOR ORTHOPEDIC APPLICATIONS

CROSS-REFERENCE TO RELATED APPLICATIONS

The present application is a nonprovisional application of U.S. Provisional Application Ser. No. 61/597,865, filed Feb. 13, 2012, the entirety of the disclosure of which is hereby incorporated by reference.

STATEMENT OF FEDERALLY SPONSORED RESEARCH OR DEVELOPMENT

Not Applicable.

BACKGROUND OF THE INVENTION

1. Field of the Invention

The field of the invention relates generally to interbody spinal fusion implants configured to correct an angular relationship between vertebrae.

2. Description of the Related Art

Implant systems utilizing specially designed spinal instrumentation are often used in surgical procedures concerning spinal conditions. Such implants are used to correct degenerative conditions and facilitate spinal fusion while stabilizing and strengthening the spine. Spinal fusion is the joining of adjacent vertebrae through shared bone. Degenerative conditions which often require spinal fusion surgery include spondylolisthesis, chronic degenerative disc disease, traumatic fractures, and other forms of spinal instability such as scoliosis.

Degenerative conditions may lead to the spinal cord or nerve roots being squeezed as to cause difficulty with back pain, numbness or weakness in one or all extremities, difficulty with instability and gait, as well as clumsiness and proprioception. In extreme cases, certain degenerative conditions can also lead to losing control over the bladder or bowels.

Implant systems used in spinal fusion surgery can be summarized into the following groups: rods; pedicle screws; hooks; plates; and interbody cages. Rods are used in conjunction with hooks and screws to immobilize involved spinal levels and to contour the spine to correct alignment. Screws are implanted into the pedicles of the spinal vertebrae to provide strong anchorage points for rods, which can then be contoured to correct deformities to facilitate spinal fusion. Hooks are used with rods and other implants to anchor them to the vertebrae. Plates, often used in the cervical spine, are designed to conform to the contour of the spine, and are held in place by screws set into adjacent vertebrae. Interbody cages are small, hollow devices packed with bone graft or other osteogenic fusion graft material (i.e., biologics) used to restore lost disc height between two vertebrae.

A problem that is encountered when using interbody cages in spinal fusion surgery is that current devices are bulky, difficult to introduce through an incision into the disc and cannot be expanded, anchored or filled with biologics in situ. Moreover, current devices are designed by engineers on a naked spine, which necessarily lacks an appreciation for the true conditions of spinal fusion surgery. For example, nerve compression, root injury, dural tears and spinal fluid leaks are frequently produced by oversized interbody cages that are significantly larger in size than the entry point allowed by the axilla of the nerve root, which may result in compression of the dorsal root ganglion.

Oversized interbody cages are often needed to accommodate a large disc space, but current devices are inserted via a small entry point, which is bordered by the spinal dura (medially), nerve root and dorsal root ganglion (cranially), pedicle (caudally), and in case of posterior lumbar interbody fusion, the residual lamina (laterally), which is usually removed when transforamenal interbody fusion is done. In some cases this can result in significant post-operative pain and/or neurologic deficit. Another problem with current devices is that they do not fully permit biologics to be injected into interbody cages in situ. Current devices also have problems with revision, adjustment and repositioning when placed in the spine, and cannot be coupled with another interbody cage in situ. Moreover, when using current devices, biologics must first be inserted into the space between the vertebral bodies, and then again inside the interbody cage after said cage is inserted into the spine. Thus, there is a need in the art for an interbody cage that has the capability to introduce biologics into an interbody cage while it is in final position in situ.

While current devices exist, in part, of other expandable cages there is still a need in the art for an expandable interbody cage that is equally concerned with both the safety and well-being of the patient and the utility of the invention. For example, some current expandable devices, when fully expanded, the devices change in length, causing screws to protrude from the interbody cage. This is a safety concern to the patient, particularly if the protruding screws are directed toward the spinal cord. Should the interbody cage then move or dislodge, it will cause a direct puncture into the spinal cord.

BRIEF SUMMARY OF THE INVENTION

Numerous interbody cages have been proposed for use in spinal fusion surgery; however, current devices are difficult to introduce into the body, require many steps for a successful insertion, contain many small parts, cannot be coupled, and are only available in limited sizes. The present invention is designed to maintain lordosis in the human spine. The interbody cage of the present invention may be expanded to fit within the disc space created by the removal of disc material between two adjacent vertebrae. The present invention is significantly easier to use than current devices because it is smaller, and can be introduced into the spine posteriorly or anteriorly in one step through a minimally invasive approach to the spine, and can then be expanded, anchored, or coupled with another interbody cage, and filled with biologics while in situ. The present invention can be coupled with another expandable interbody cage of the present invention or with a stationary cage both before placement in the body and in situ, which improves functionality and versatility over current devices. These features decrease surgical time, effort and complications. The present invention is designed to expand up to eighty percent (80%) of its initial size in one or two directions (cranially or caudally). This expandable feature allows the present invention to fit wholly in the space created by the removal of the disc material between two adjacent vertebrae, without the need to first inject biologics into the space between the vertebral bodies.

Because the present invention has the ability to be distracted and anchored while it situ, it provides an increase of the foramenal size; hence, a better decompression of the nerve root, and also a decreased incidence of dislodgment in the immediate post-operative period. The ability to introduce biologics in the present invention solely after it is expanded decreases the dead space left within the interbody cage, and improves the contact of the biologics with the endplates, which ultimately may result in improved fusion rates.

The ability to couple the interbody cage in situ with either another expandable or a fixed-length interbody cage also provides options for designing longer anterior constructs via a posterior approach. In addition, the present invention can also be readily re-engaged, adjusted or removed, depending on the specific surgical need, and has a thirty percent (30%) wider foot print than current devices in the medio-lateral direction.

The present invention is useful in the cervical, thoracic and lumbar areas of the spine; however, said invention may only be introduced into the cervical spine through an anterior approach. In the thoracic and lumbar spine, the present invention may be introduced through a posterior, posterolateral, lateral or strait anterior approach. In the lumbar spine, the present invention may be manipulated while under the dural surface because the entry point can be wider in lateral direction and narrower craniocaudally. This permits the present invention to be of a rectangular shape rather than a square shape, thus allowing safer and better retraction of the dura medially. This in turn allows the device to have a wider foot print on the disc endplate, as well as more space to place biologics in the cage. As the cage is expanded in situ, the separation results in increased foramenal width, hence better decompression of the neural elements.

Accordingly, one embodiment of the present invention comprises spinal fusion intervertebral implant that includes an insertion/injection handle; a threaded rod; an interbody cage with upper and lower body portions; a screw; a horizontal slotted wedge; and two vertical sliding tapped wedges, such that in elevational side view, the present invention has the shape of a bullet. In an alternative embodiment of the present invention for the dual expansion feature, the interbody cage is comprised of an additional horizontal slotted wedge.

The insertion/injection handle of the present invention is a hollow tube with a long internal allen or star-shaped shaft designed to accept a threaded rod. The insertion/injection handle has, at one end, a knurled top and threaded collar. The opposing end of the insertion/injection handle may have a male-threaded fitting, with an internal female-thread, to allow the insertion/injection handle to achieve a flush attachment to a threaded collar on one end of the interbody cage. In an alternative embodiment, the opposing end of the insertion/injection handle may have a female-threaded fitting, with an internal male-thread to achieve a flush attachment to the interbody cage. In some embodiments, the insertion/injection handle can be packaged with the interbody cage preloaded on the insertion/injection tool.

The threaded rod of the present invention is a long allen or star-shaped shaft, which is inserted into the insertion/injection handle and used as a screwdriver to rotate a screw within the interbody cage. The threaded rod has, at one end, a knurled top to allow rotation by hand or external tool. The opposing end of the threaded rod terminates with a depression on the top of the screw, located within the interbody cage.

The interbody cage is the body of the present invention, and can be fabricated from any material, including surgical metals, plastics or human bone, with PEEK being the preferred embodiment. It is not preferable that the interbody cage be fabricated from titanium because this material does not permit orthopedic surgeons to assess the endplate bone growth in order to assess the fusion rate. As compared to current devices fabricated from titanium, the present invention will provide the benefit of better fusion rates because PEEK allows it to be more pliable, which makes its elasticity resemble that of human bone.

The interbody cage is a rectangular structure of uniform height in elevation view, with a trapezoid-shaped bullet nose on the leading end of said cage. The interbody cage has no solid upper or lower surface, which, in plan-view, exposes the screw within that operates the horizontal and vertical wedges. The interbody cage is designed to allow for movement of opposing horizontal and vertical wedges within said cage from the rotation of a screw which is pre-fixed inside said cage. The opposing end of the interbody cage has a threaded collar designed to attach to the insertion/injection handle. From plan-view, the opposing end of the interbody cage reveals the head of the screw.

The dimensions of the interbody cage vary, depending on whether the present invention is implanted in the cervical, thoracic, or lumbar spine, and whether the interbody cage is collapsed, partially expanded, or fully expanded. The interbody cage used in the cervical spine will have a depth and width range of 10-20 mm and a height range of 5-10 mm. The interbody cage used in the thoracic spine will have a depth and width range of 15-30 mm and a height range of 7-18 mm. The interbody cage used in the lumbar spine will have a depth range of 20-35 mm, a width range of 10-40 mm, and a height range of 7-18 mm.

The interbody cage has two embodiments, allowing said cage to expand in one direction or two opposing directions. In its fully expanded position, the interbody cage can be of any shape or width to accommodate the disc space between two vertebral bodies, to maintain or correct lordosis. The interbody cage may also have tabs or key holes on either side adjacent to the leading or opposing end of said cage to couple with other expandable or fixed interbody cages to allow for further expansion.

The screw of the present invention is solid, fabricated from titanium, and has an allen or star-shaped depression on the head of said screw that attaches to the end of the threaded rod. The screw is threaded through openings in both vertical sliding tapped wedges located within the interbody cage. The screw is secured with a threaded collar at one or both ends such that it can only be rotated, but not move vertically. The screw runs the entire length of the interbody cage and penetrates the nose of the interbody cage. The leading end of the screw is flattened to maintain its horizontal position in the interbody cage when being rotated by the threaded rod.

The horizontal slotted wedge of the present invention is a slotted wedge that is free to lift from the body of the interbody cage as said wedge is displaced by the vertical sliding tapped wedges. The horizontal slotted wedge has internal stop pins that cause said wedge to stop moving at its maximum expansion, as to prevent said wedge from fully separating from the cage. The depth, shape and slope of the horizontal slotted wedge are variable to achieve an almost infinite range of adjustment. The edges of the horizontal slotted wedge that ultimately make contact with the vertical sliding tapped wedges are channeled or serrated to account for friction. In an alternative embodiment of the interbody cage for dual expansion, two horizontal slotted wedges are provided that travel in opposing directions.

The vertical sliding tapped wedges of the present invention are wedges, fabricated from titanium, situated in opposing ends of the interbody cage with threaded openings configured to accept the screw, which is pre-fixed inside said cage. The vertical sliding tapped wedges are configured to face each other, and are generally sloped at the top so as to create an angle when contacting the horizontal slotted wedge. The vertical sliding tapped wedges will thread onto the screw to a maximum position of halfway down the screw. The vertical sliding tapped wedge located nearest the leading edge of the cage is reversed tapped to permit said wedge to move towards the opposing wedge as the screw is rotated by the threaded rod. The depth, shape and slope of the vertical sliding tapped wedges are variable. The edges of the vertical tapped sliding wedges that ultimately make contact with the horizontal wedge is channeled or serrated to account for friction.

In the performing of a an interbody spinal fusion posteriorly with the present invention, a nurse or surgeon attaches the insertion/injection handle to the threaded collar on a fully collapsed interbody cage by rotating said handle until it becomes flush with the opposing end of the interbody cage. In an alternative embodiment, the nurse or surgeon would first attach additional expandable or fixed interbody cages to the initial interbody cage by coupling said cages together utilizing the tabs or key holes on the initial cage.

The threaded rod is then inserted through the hollow opening of the insertion/injection handle, and aligned with the depression in the head of the screw. The surgeon then places the interbody cage through the incision and in the preferred location within the spine, causing only minimal trauma to the surrounding soft tissue of neural structures. Once in place, the threaded rod is then rotated to operate the screw within the interbody cage.

The nurse or surgeon confirms that the interbody cage is in the correct location by use of internal, external and radiographic markers. As the screw rotates, the horizontal and vertical wedges within the interbody cage are operated. As the screw rotates, the vertical sliding tapped wedges on both ends of the interbody cage are forced closer together, gradually displacing the horizontal slotted wedge, which then moves in a ninety degree direction as it expands one edge of said cage outward.

Since there is sometimes a need to anchor the cage rather than just expand it, instead of deploying a flat surface or a ring, the present invention can also be anchored by deploying a set of anchoring pins 3 mm or more in length, craniocaudally. This can be utilized in all areas of the spine. The fact that the present invention has the ability to self-anchor means that it can be used in the thoracic and lumbar spine with all of the available approaches (i.e., posterior, anterior, lateral).

If the interbody cage is expanded too far, the threaded rod is turned in the opposite direction, gradually releasing the vertical sliding tapped wedges to permit compression of the edge of said cage that expanded. Once the screw is fully engaged within the interbody cage to create the desired expansion by operating the horizontal and vertical wedges, the threaded rod is released from the depression on the head of the screw and removed from the hollow insertion/injection handle.

The surgeon then uses a syringe to insert biologics down the hollow shaft of the insertion/injection handle. The biologic material can be of surgeon's choice: bone, healos, DBM, BMP, allograft, autograft, etc. The biologics flow down the hollow shaft of the insertion/injection handle and enters the interbody cage through the threaded collar at the opposing end of said cage. The channeled or serrated feature of the horizontal and vertical wedges permits biologics to pass between said wedges. Once the interbody cage is sufficiently full of biologics, the surgeon unthreads the insertion/injection handle from the threaded collar at the opposing end of the interbody cage, and removes from said cage from the incision.

In the performing of an interbody spinal fusion anteriorly with the present invention, the procedure will be largely simplified as there will be no need to remove the antero-lateral osteophytes. This requires less usage of electrocaurery, which will potentially diminish the risk of injury to the posterior pelvic plexus and the rate of retrograde ejaculation. Also the need for less dissection and retraction needed on the major vessels (i.e., aorta/vena cava) will decrease the risk of injury to these structures. The ease of insertion of the device into the intervertebral space will improve as the device will fit in a narrow or collapsed position and then anchor itself and expand in situ which will diminish the need for mechanical persuasion (i.e., hammering the device in) and again at this point the dead space created by expanding the cage will be filled with biologic in situ.

Once expanded in situ, the present invention has the ability to auto-adjust to the lordosis or kyphosis of the spine up to twelve (12) degrees in the antero-posterior direction. Those skilled in the art will appreciate the auto-adjustment feature, as current devices typically consist of parallel endplates that are never a precise, anatomically correct fit.

It is an object of the present invention to provide a spinal interbody cage that is introduced into the spine with a minimally-invasive approach that reduces risk of injury, post operative pain and/or neurologic deficit in patients.

It is another object of the present invention to provide a spinal interbody cage that is easy to use in any surgeon's hands, simple and self-explanatory in a one step approach.

It is yet another object of the present invention to provide a spinal interbody cage that is expandable up to eighty percent (80%) of its initial size in situ.

It is yet another object of the present invention to provide a spinal interbody cage that has a thirty percent (30%) wider foot print than current devices.

It is yet another object of the present invention to provide a spinal interbody cage that is self-anchoring within the spine.

It is yet another object of the present invention to provide a spinal interbody cage that can be inserted into the spine from a posterior or anterior approach.

It is yet another object of the present invention to provide a spinal interbody cage that can be coupled with another expandable or fixed-length interbody cage in situ.

It is yet another object of the present invention to provide a spinal interbody cage that can be inserted into the spine without first injecting biologics into the space between two vertebral discs.

DETAILED DESCRIPTION OF THE INVENTION

Figure 1:
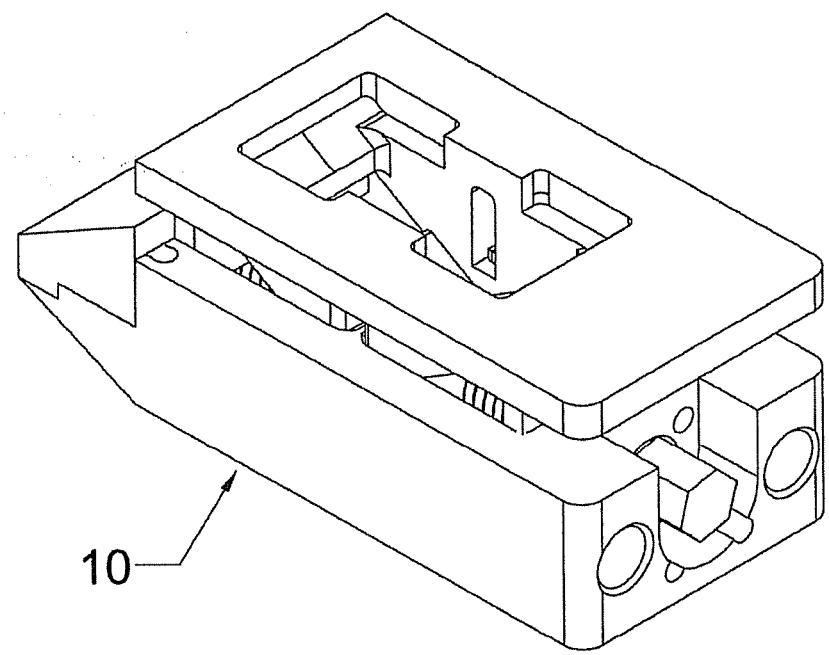
FIG. 1 is a perspective view of the expandable interbody cage in an expanded state. Applicants hereby suggest that FIG. 1 be included on the front page of the patent application publication and the patent.
Figure 2:
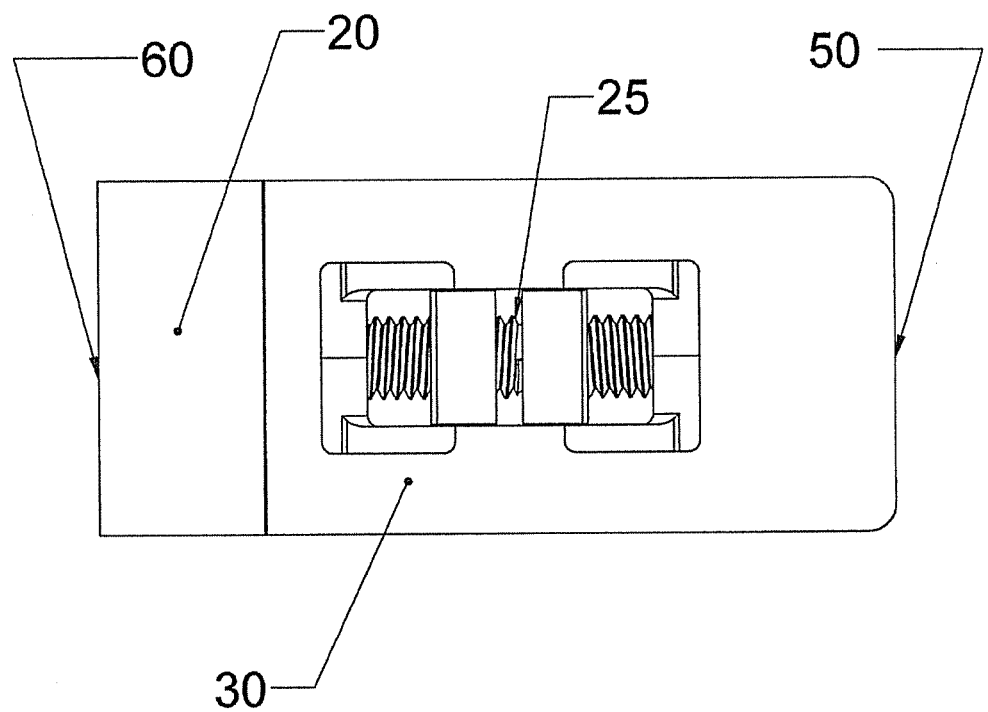
FIG. 2 is a top view of the expandable interbody cage shown in FIG. 1 in an expanded state.
Figure 3:
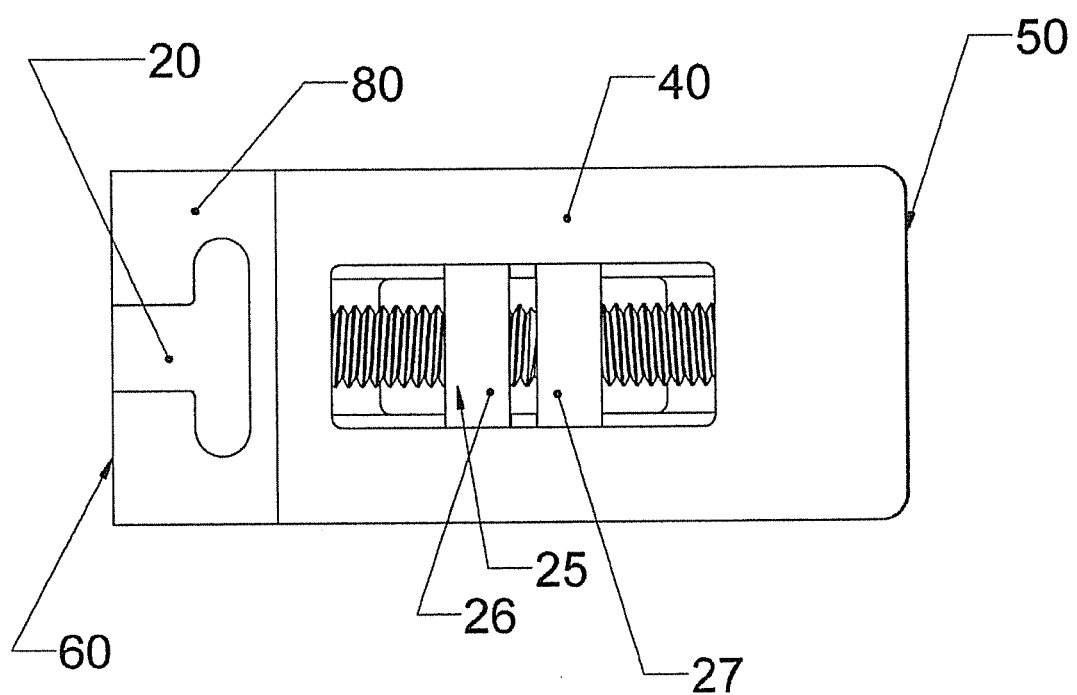
FIG. 3 is a bottom view of the expandable interbody cage shown in FIG. 1 in an expanded state.
Figure 4:
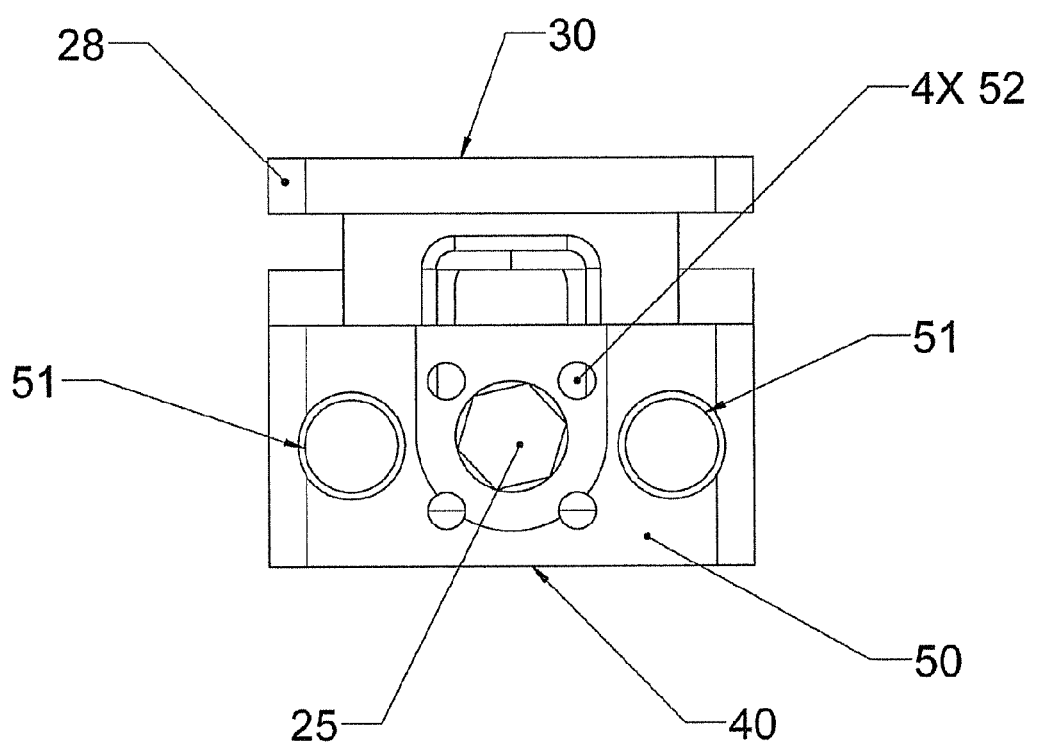
FIG. 4 is a side elevation view of the trailing end of the expandable interbody cage shown in FIG. 1 in an expanded state.
Figure 5:
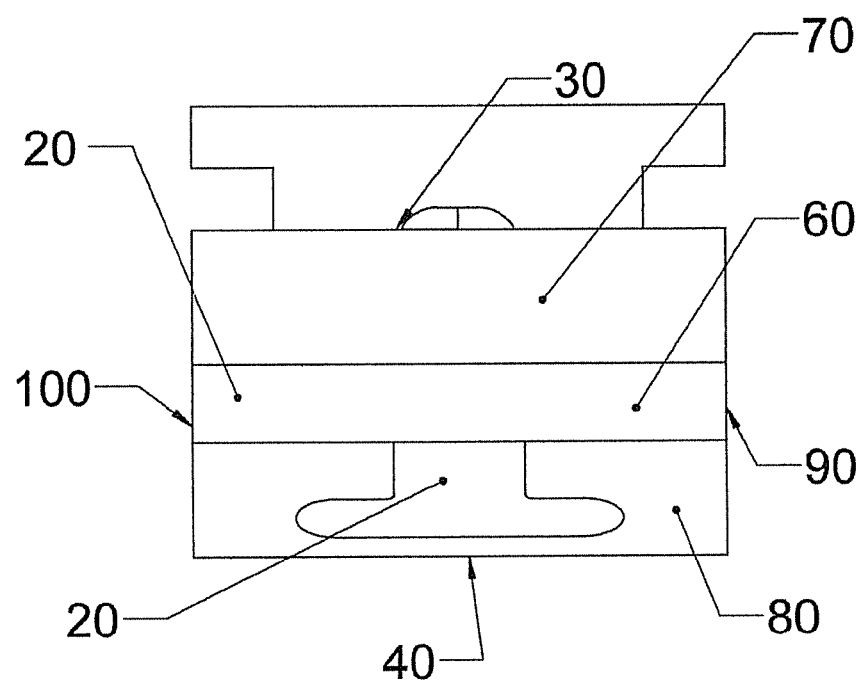
FIG. 5 is a side elevation view of the leading end of the expandable interbody cage shown in FIG. 1 in an expanded state.
Figure 6:
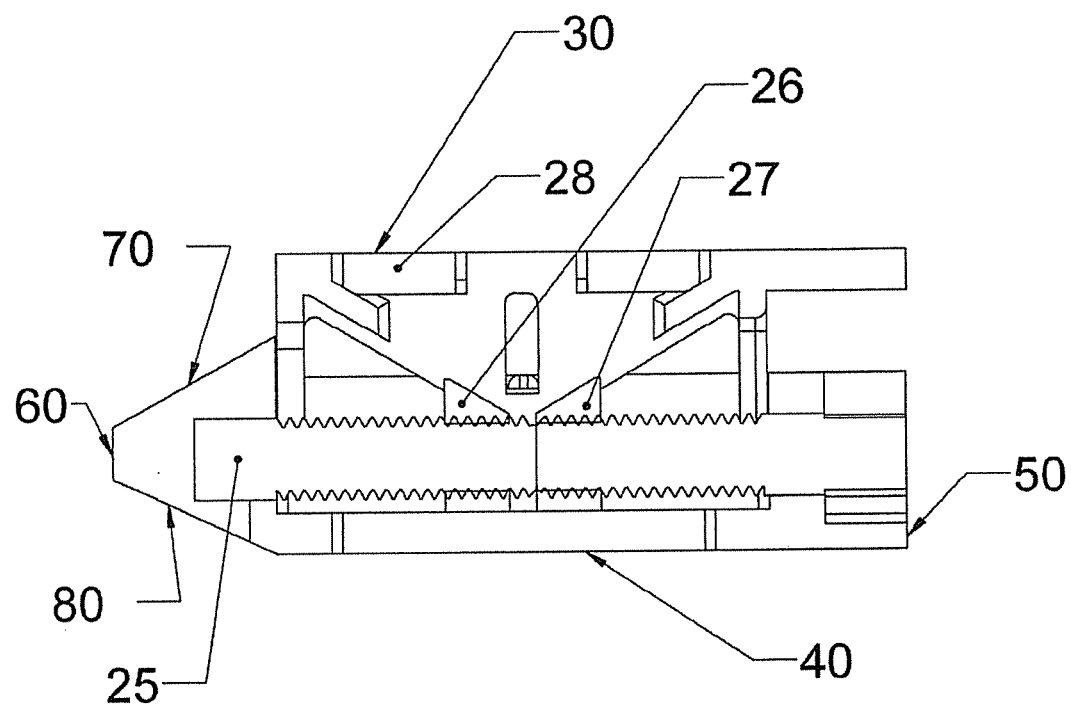
FIG. 6 is a side cross-sectional view of the expandable interbody cage shown in FIG. 1 in an expanded state.

Various height change mechanisms of the expandable interbody cage 10 can be used to properly space adjacent vertebrae in the spine. Referring to FIGS. 1 through 5, the expandable interbody cage 10 is shown, which generally has a rectangular configuration with a flat top surface 30, a flat bottom surface 40 and a flat leading end 60 bullet nose 20 in a trapezoidal configuration with solid surfaces 60, 70, and 80, as shown in FIGS. 5 and 6. In the preferred embodiment, the top surface 30 is parallel to the bottom surface 40, while the expandable interbody cage 10 is an unexpanded or slightly expanded state, as shown in FIGS. 4 and 5. The top surface 30 and the bottom surface 40 form a support structure for bearing against adjacent vertebrae and when in a fully expanded state commensurate with the needs of a patient, the expandable interbody cage 10 creates an angular relationship is created that maintains the desired lordosis of the human spine. Referring to FIG. 3, in the preferred embodiment, the top surface 30 and the bottom surface 40 are not solid, but rather, both have a 14 mm×6 mm rectangular opening that exposes the screw 25 and the vertical tapped sliding wedges 26 and 27, within. This hollow opening provides for bone growth to occur from the vertebrae through the openings to the internal chamber of the expandable interbody cage 10 after biologics are injected while in situ. The injection of the biologics into the expandable interbody cage 10 serves to promote bone growth.

As shown in FIG. 4, the trailing end 50 of the expandable interbody cage 10 is a flat surface with two penetrations 51 with 3 mm diameter that are configured to accept an insertion tool that is used to place the expandable interbody cage 10 in situ. In the preferred embodiment, the trailing end 50 is also configured with four penetrations 52 of 1.5 mm in diameter, which permit biologics to flow from the insertion tool into the interior of the expandable interbody cage 10. It should be appreciated that although the penetrations 51, 52 at the trailing end 50 are generally round in configuration, it is within the scope of the present invention that the penetrations 51, 52 may have any size, shape, configuration, and distribution suitable for the present invention's intended purpose. The screw 25 is 3 mm in diameter and accessed and rotated via the trialing end 50 by use of a threaded rod, which, when rotated, activates the vertical tapped sliding wedges 26, 27 to create an angular relationship with the horizontal slotted wedge 28, to force said wedge to expand from the expandable interbody cage 10 to any height in its preferred embodiment of 5-18 mm.

Figure 11:
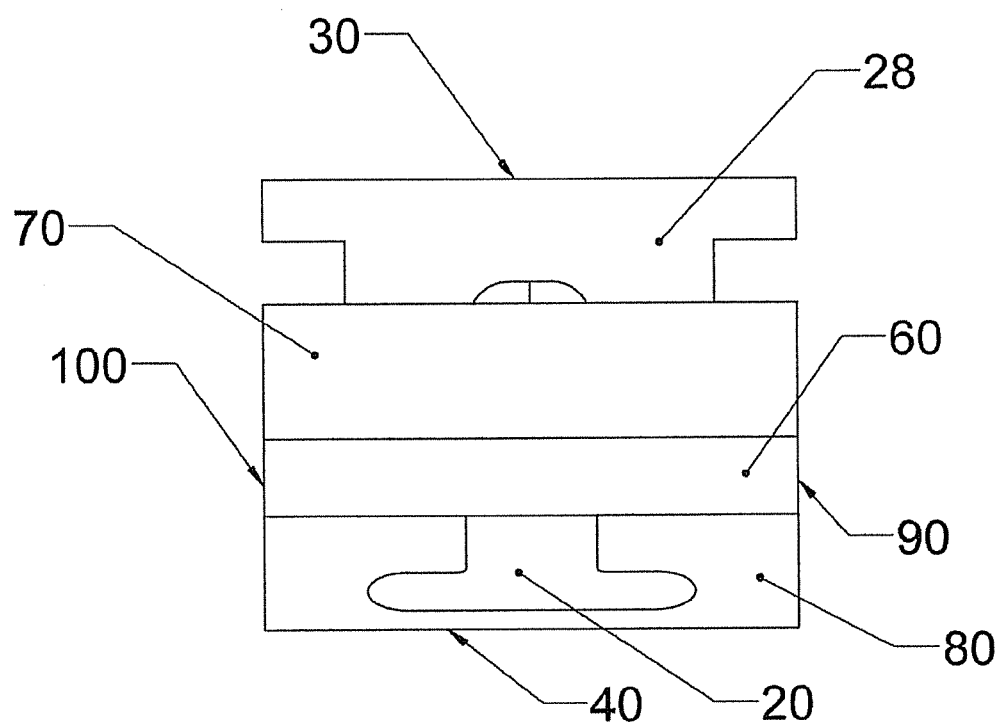
FIG. 11 is a side elevation view of the leading end of the expandable interbody cage shown in FIG. 1 in an expanded state.
Figure 12:
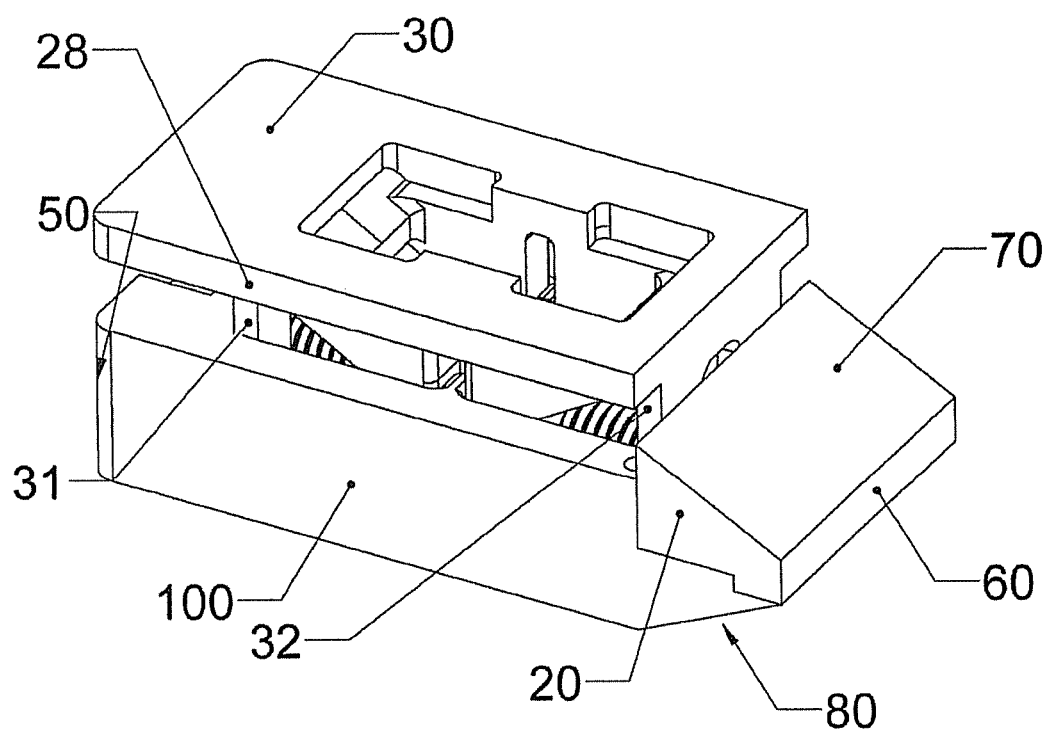
FIG. 12 is a perspective view of the expandable interbody cage shown in FIG. 1 in an expanded state.
Figure 30:
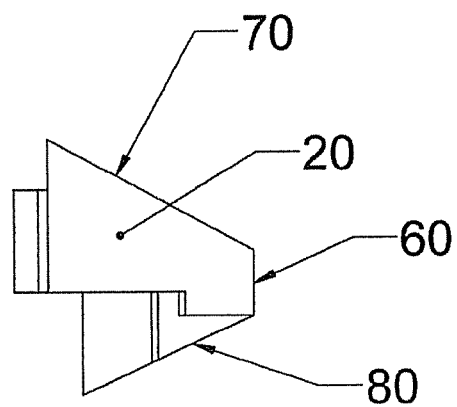
FIG. 30 is a side elevation view of an embodiment of the leading end of the expandable interbody cage shown in FIG. 29.
Figure 31:
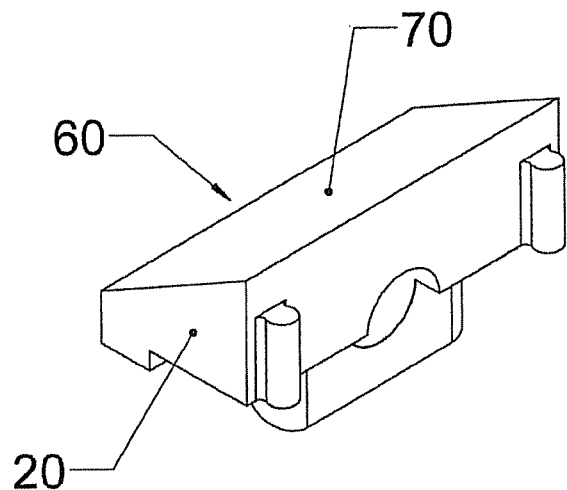
FIG. 31 is a perspective view of an embodiment of the leading end of the expandable interbody cage shown in FIG. 29.
Figure 32:
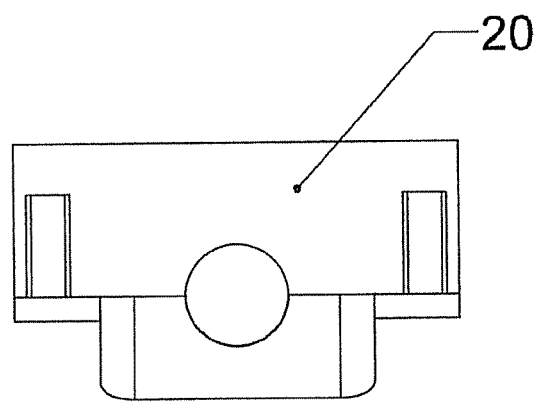
FIG. 32 is a side elevation view of an embodiment of the leading end of the expandable interbody cage shown in FIG. 29.

Referring to FIGS. 5 and 11, the sides 90 and 100 of the expandable interbody cage 10 are solid rectangular shapes that are configured to be parallel. Referring to FIG. 6, a side cross-sectional view is shown. The assembly process for the present invention commences with installing the vertical sliding tapped wedges 26 and 27 on the screw 25. The screw/wedge assembly 25, 26, 27 is then inserted into the body of the expandable interbody cage 10, with the screw 25 protruding the tailing end 50 of the expandable interbody cage 10. As later shown in FIG. 30, the bullet nose 20 is then pressed onto the expandable interbody cage 10. The screw/wedge assembly 25, 26, 27 then gets inserted into to bullet nose 20, with the vertical sliding tapped wedges 26, 27 positioned into the closed position. To install the horizontal slotted wedge 28, the present invention must be turned onto its side, where said wedge 28 is inserted into one side of the expandable interbody cage 10 and over the screw 25. The horizontal slotted wedge 28 can then be snapped into the body of the expandable interbody cage 10.

Referring again to FIG. 6, the screw 25 is designed to penetrate the bullet nose 20 of the leading end 60, which, when rotated, causes the vertical tapped sliding wedges 26, 27 to converge towards the center of the expandable interbody cage 10, which in turn, activates the horizontal slotted wedge 28. The horizontal slotted wedge 28 expands with the convergence of the vertical tapped sliding wedges 26, 27 either until the desired height is achieved or the wedges 26, 27 reach their maximum convergence point wherein the horizontal slotted wedge 28 is fully expanded to its maximum height of 18 mm.

Figure 7A:
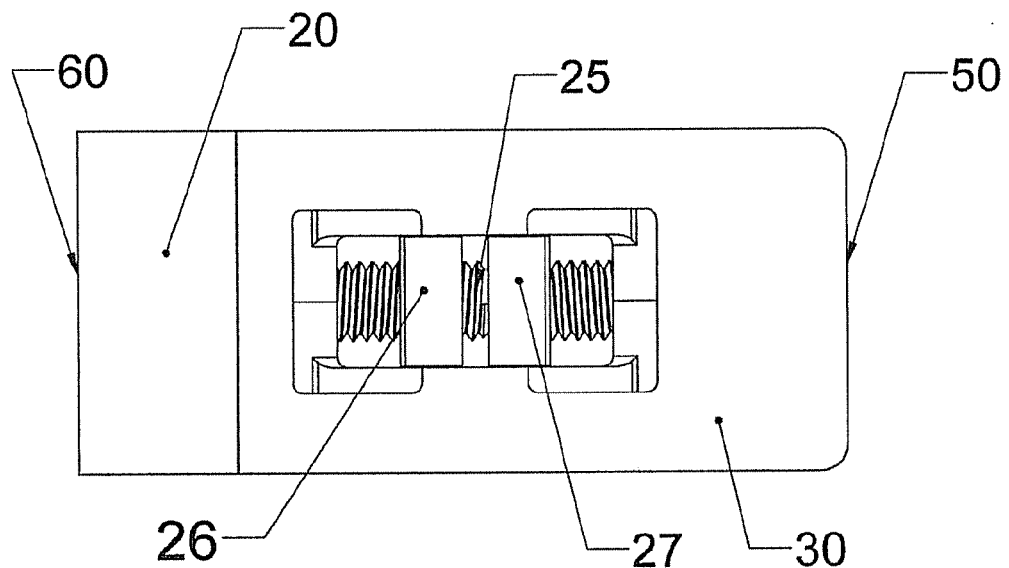
FIG. 7A is a top view of the expandable interbody cage shown in FIG. 1 in an expanded state.
Figure 7B:
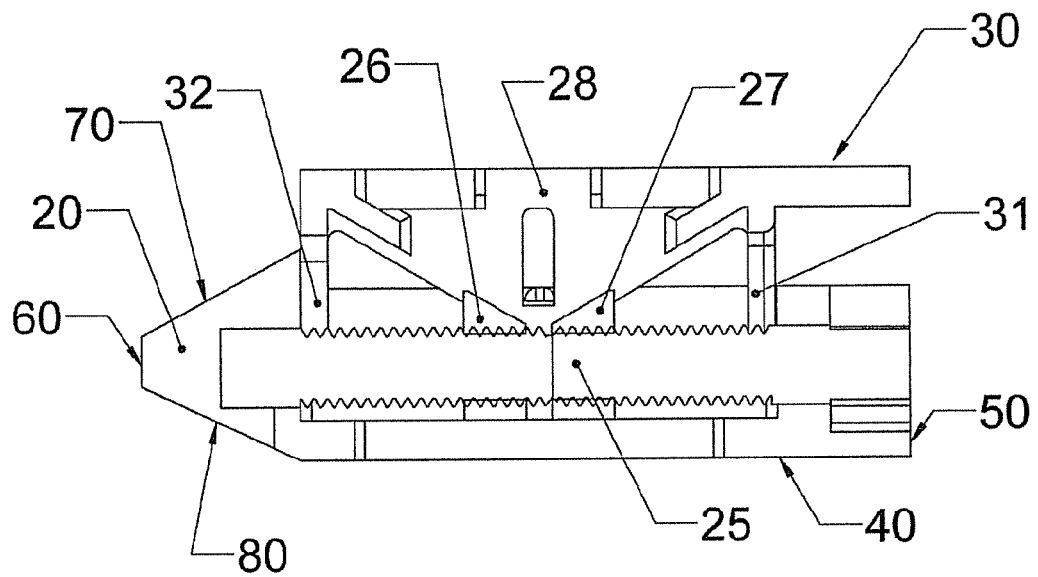
FIG. 7B is a side cross-sectional view of the expandable interbody cage shown in FIG. 7A in an expanded state.
Figure 8:
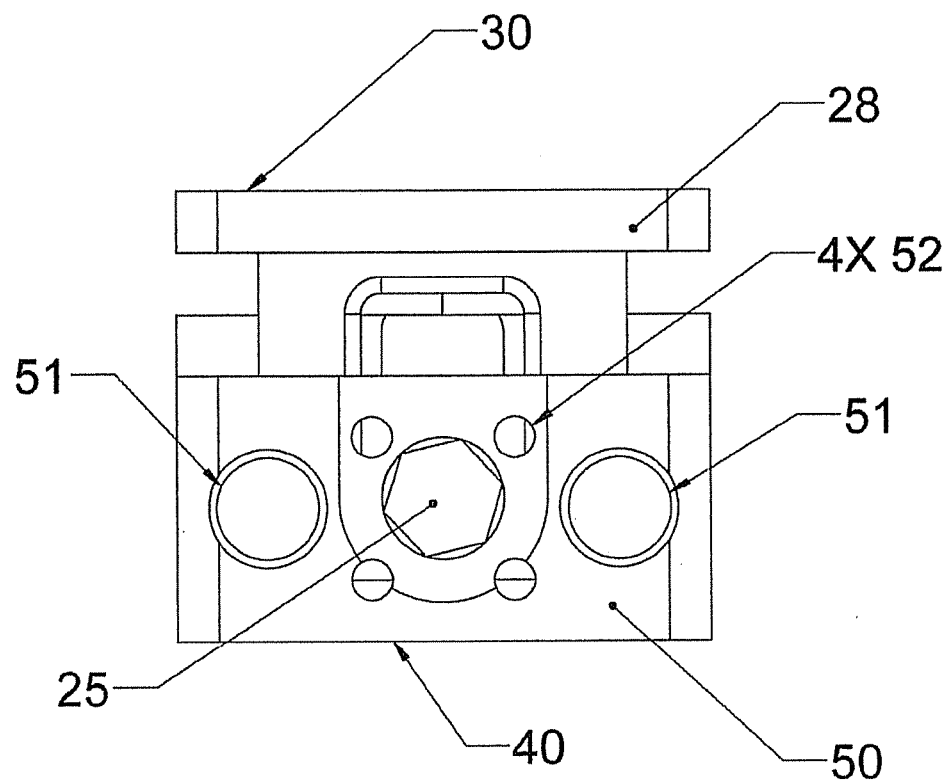
FIG. 8 is a side elevation view of the trailing end of the expandable interbody cage shown in FIG. 1 in an expanded state.
Figure 9:
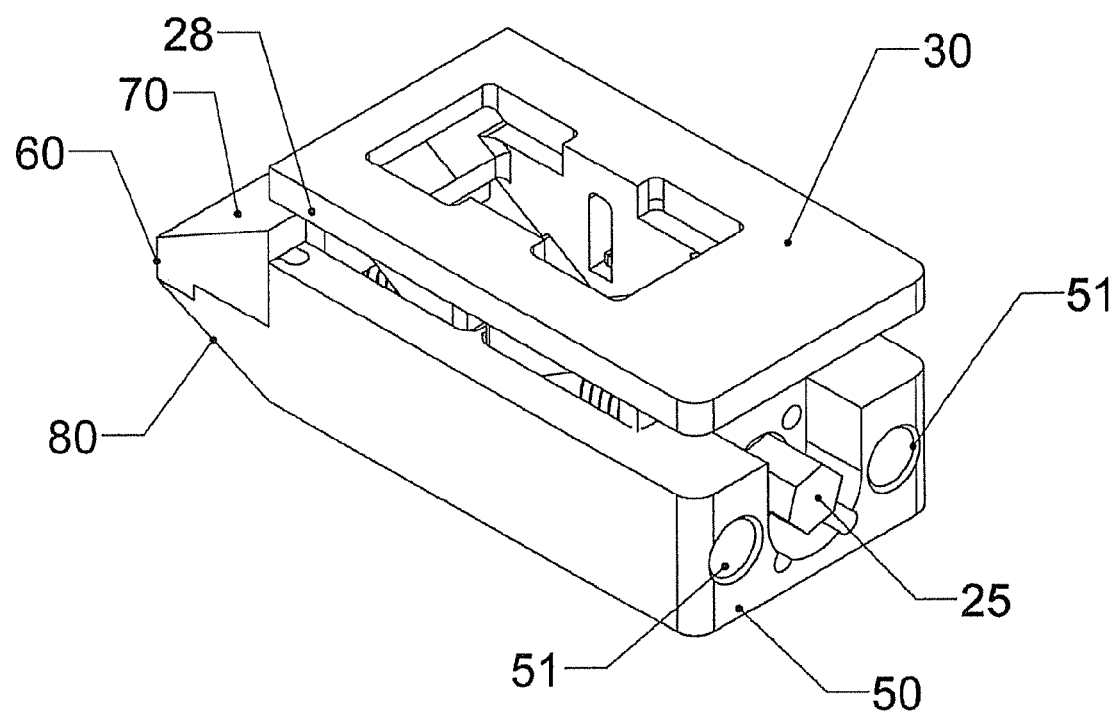
FIG. 9 is a perspective view of the expandable interbody cage shown in FIG. 1 in an expanded state.
Figure 10A:
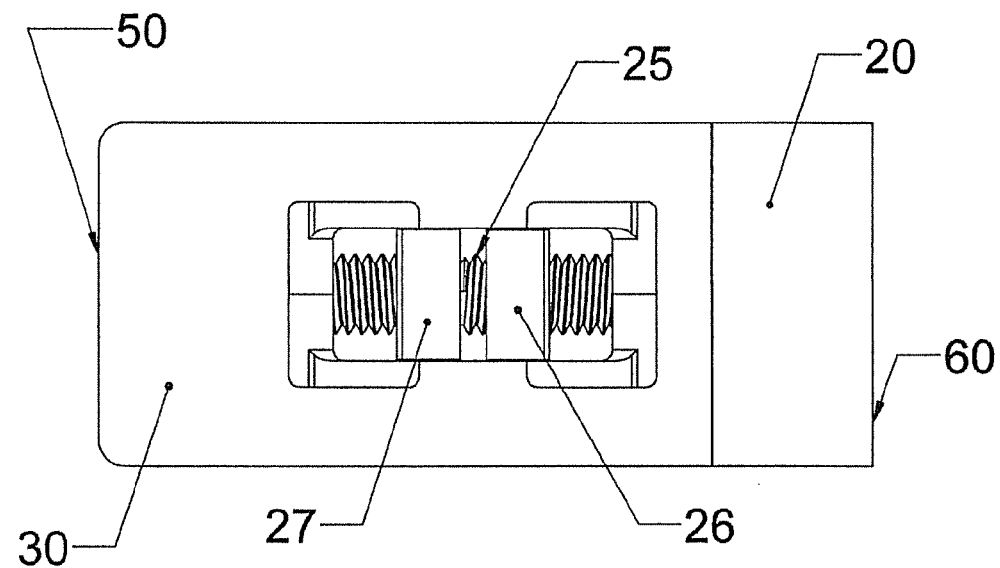
FIG. 10A is a top view of the expandable interbody cage shown in FIG. 1 in an expanded state.
Figure 10B:
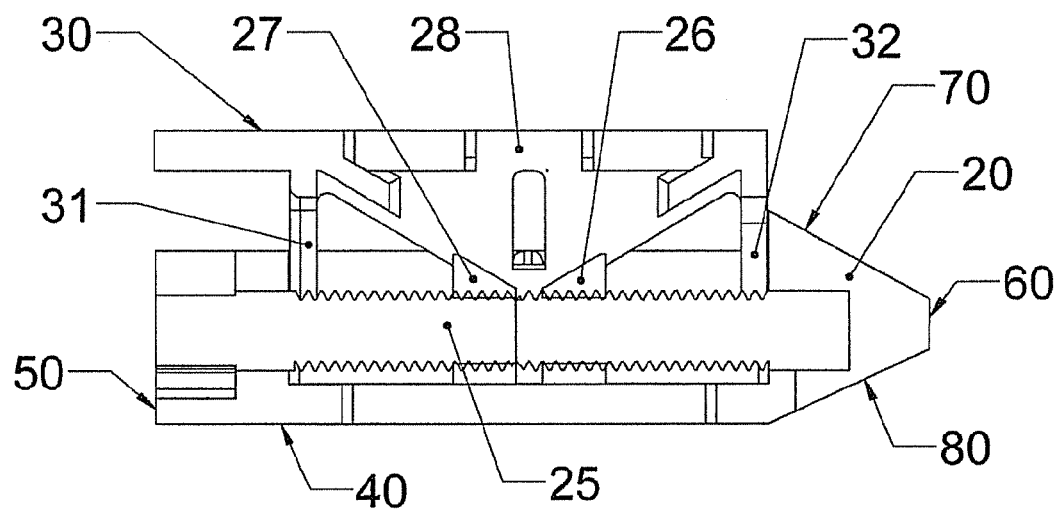
FIG. 10B is a side cross-sectional view of the expandable interbody cage shown in FIG. 10B in an expanded state.

Referring to FIGS. 7B and 10B, a cross-sectional view is shown that depicts the horizontal slotted wedge 28 at its maximum height. In use, the expandable interbody cage 10 is implanted in the body in an unexpanded state. As the threaded rod is engaged with the screw 25 from the trailing end 50, causing the vertical tapped sliding wedges 26, 27 to converge, the risers 31, 32, of the horizontal slotted wedge 28 converge upward until the desired expansion height is achieved.

Figure 13:
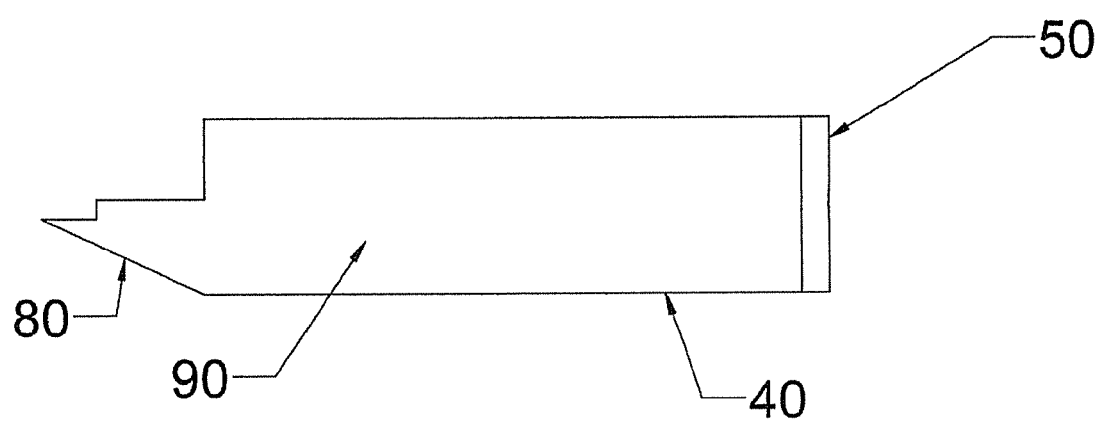
FIG. 13 is a side elevation view of the expandable interbody cage shown in FIG. 1, wherein the leading end and expandable horizontal wedge of said cage is not shown.
Figure 14:
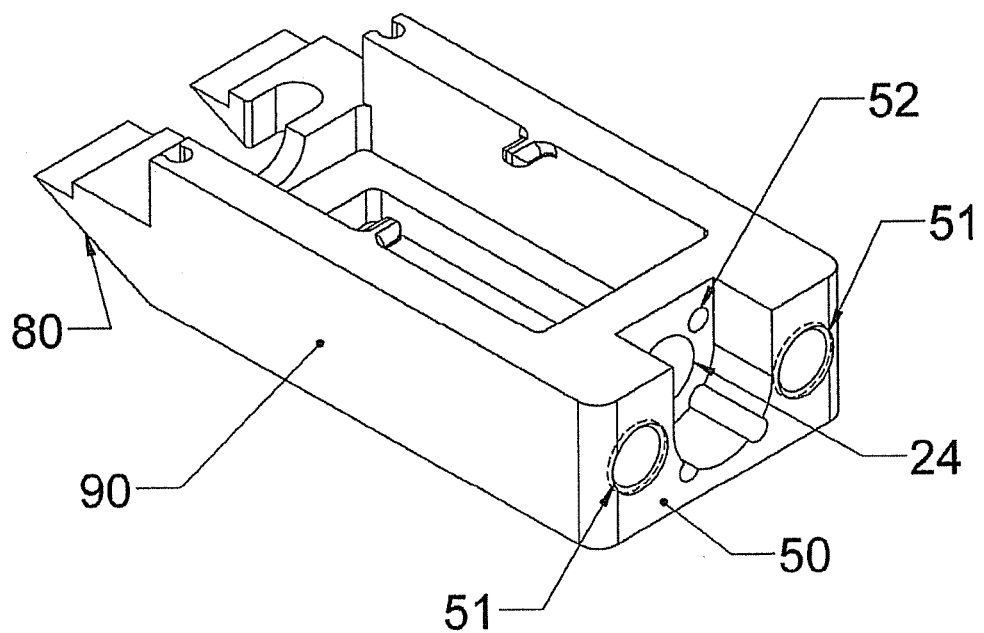
FIG. 14 is a perspective view of the expandable interbody cage shown in FIG. 13

Referring to FIGS. 13 and 14, the expandable interbody cage 10 is shown, wherein the leading end 60, bullet nose, 20, expandable horizontal wedge 28, vertical tapped sliding wedges 26, 27, and screw 25 are not shown. Those skilled in the art will appreciate the ease of assembly of the expandable interbody cage 10, with all of its component parts which may be attached while said cage is laying on its side 90 or 100. Referring specifically to FIG. 14, there is an opening at the trailing end 50 of the expandable interbody cage 10 that is designed to accept the screw 25 that operates the vertical tapped sliding wedges 26, 27 and the horizontal slotted wedge 28.

Figure 15:
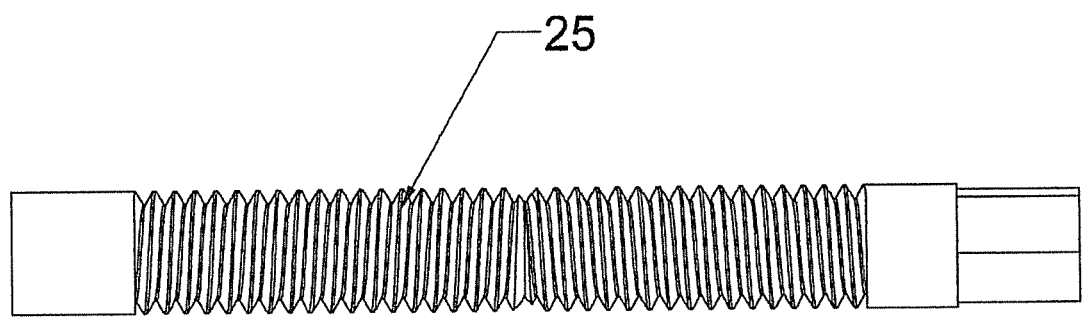
FIG. 15 is an enlarged view of an embodiment of the screw inner member of the expandable interbody cage.
Figure 16:
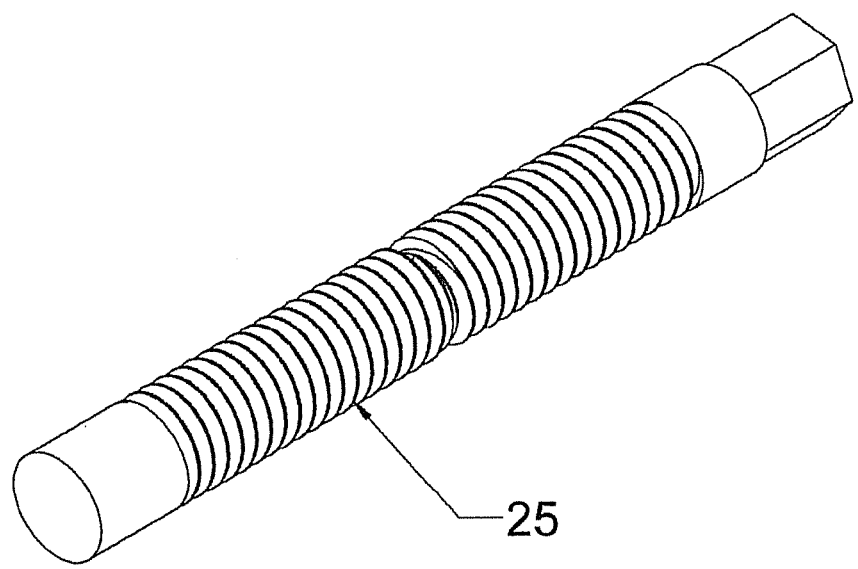
FIG. 16 is a perspective view of an embodiment of the screw inner member of the expandable interbody cage.
Figure 17:
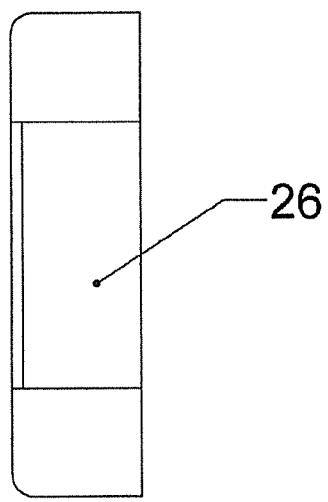
FIG. 17 is a top view of an embodiment of a vertical tapped sliding wedge inner member of the expandable interbody cage.
Figure 18:
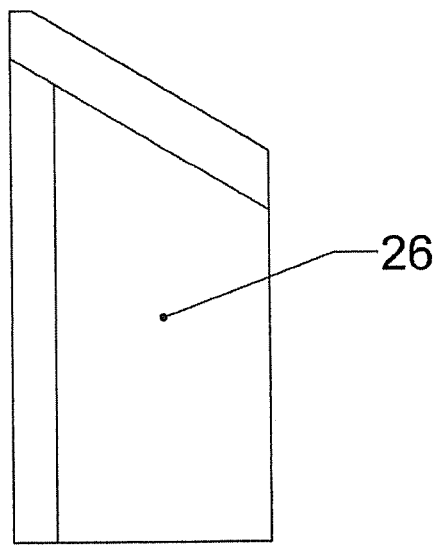
FIG. 18 is a side elevation view of an embodiment of a vertical tapped sliding wedge inner member of the expandable interbody cage shown in FIG. 17.
Figure 19:
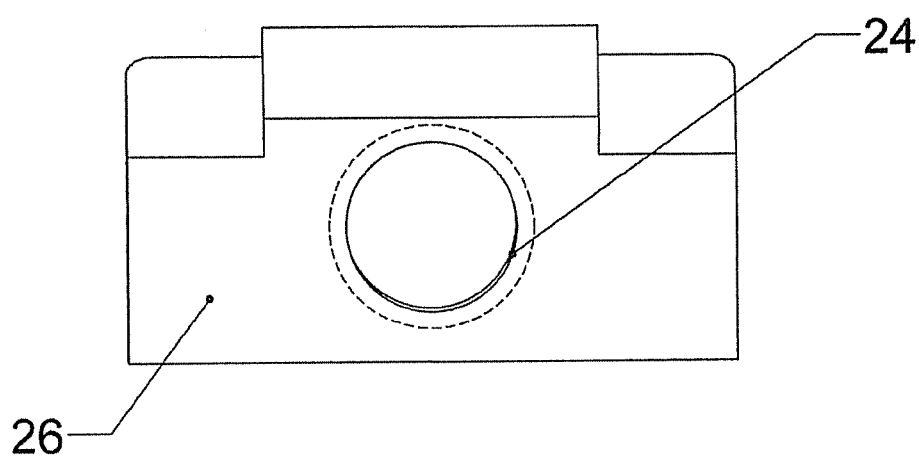
FIG. 19 is a side elevation view of an embodiment of a vertical tapped sliding wedge inner member of the expandable interbody cage shown in FIG. 17.
Figure 20:
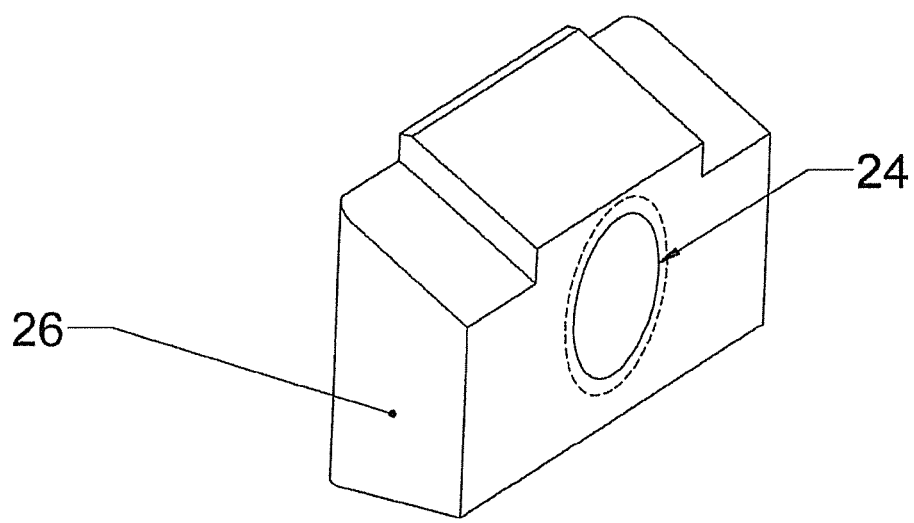
FIG. 20 is a perspective view of an embodiment of a vertical tapped sliding wedge inner member of the expandable interbody cage shown in FIG. 17.
Figure 21:
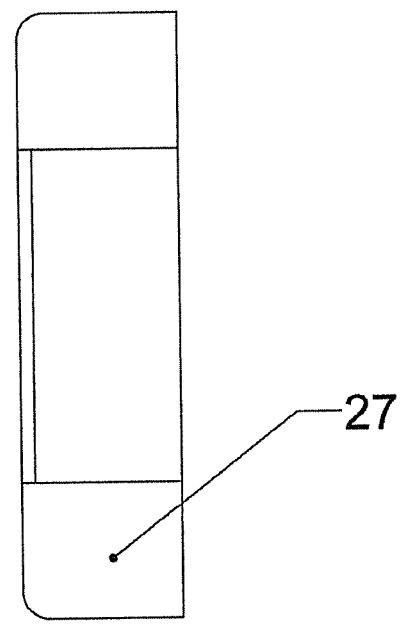
FIG. 21 is a top view of an embodiment of a vertical tapped sliding wedge inner member of the expandable interbody cage.
Figure 22:
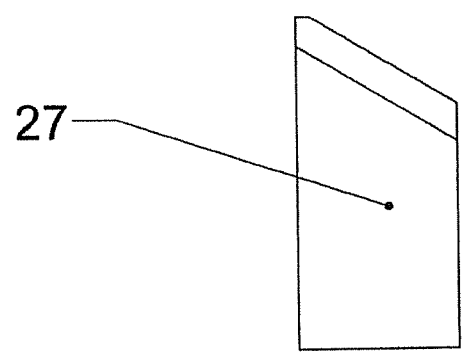
FIG. 22 is a side elevation view of an embodiment of a vertical tapped sliding wedge inner member of the expandable interbody cage shown in FIG. 21.
Figure 23:
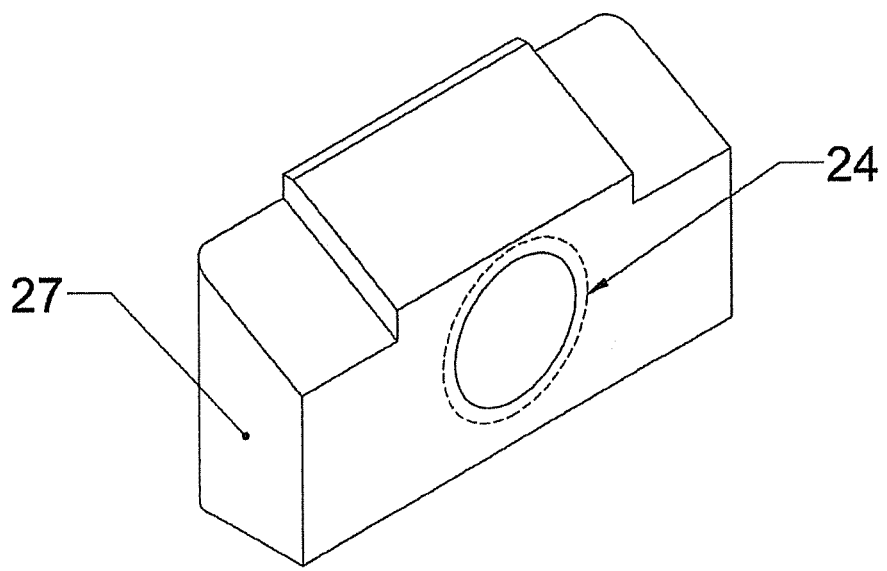
FIG. 23 is a perspective view of an embodiment of a vertical tapped sliding wedge inner member of the expandable interbody cage shown in FIG. 21.
Figure 24:
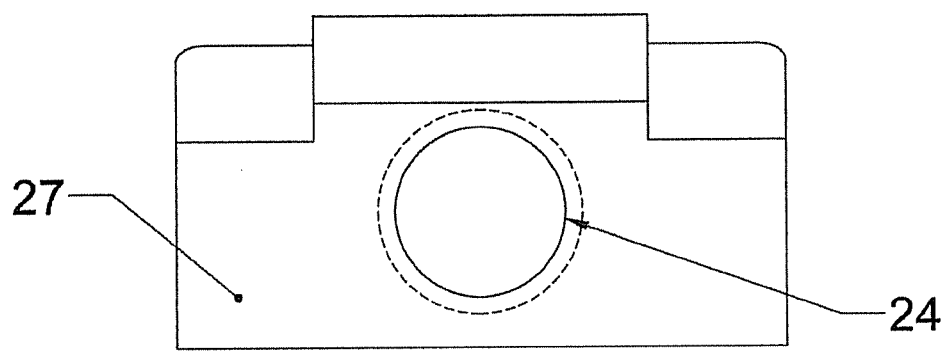
FIG. 24 is a side elevation view of an embodiment of a vertical tapped sliding wedge inner member of the expandable interbody cage shown in FIG. 21.
Figure 25:
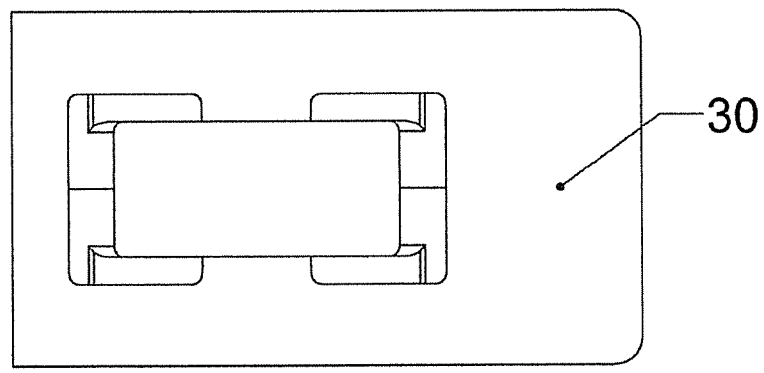
FIG. 25 is a top view of an embodiment of the expandable horizontal wedge of the expandable interbody cage shown in FIG. 1.
Figure 26:
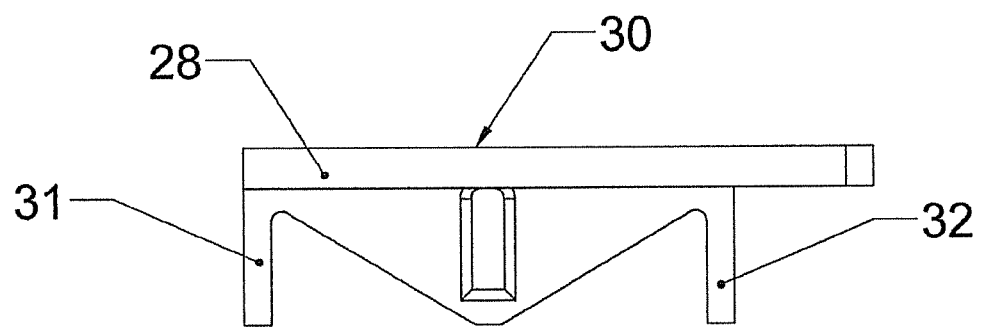
FIG. 26 is a side elevation view of an embodiment of the expandable horizontal wedge of the expandable interbody cage shown in FIG. 25.
Figure 27:
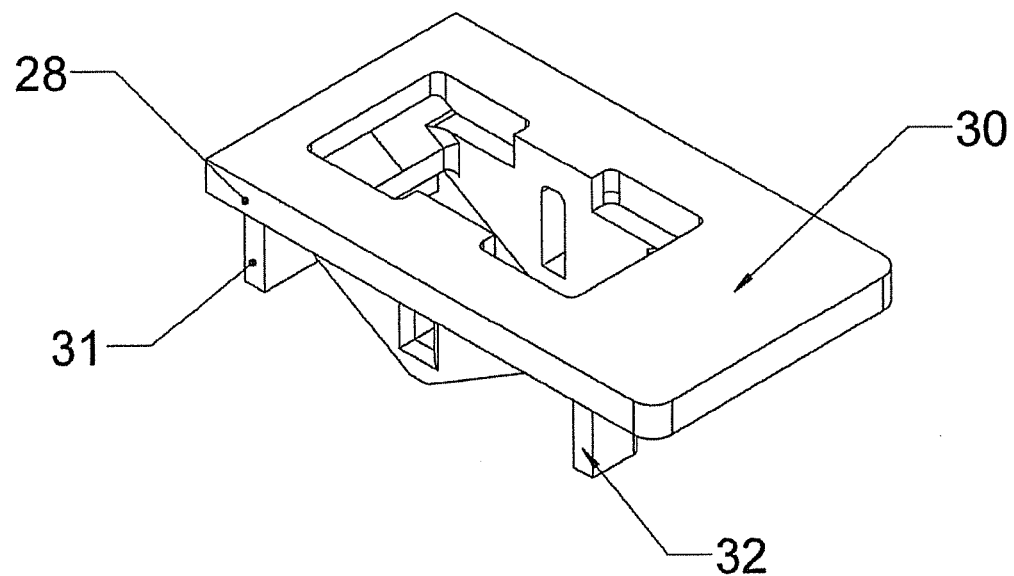
FIG. 27 is a perspective view of an embodiment of the expandable horizontal wedge of the expandable interbody cage shown in FIG. 25.
Figure 28:
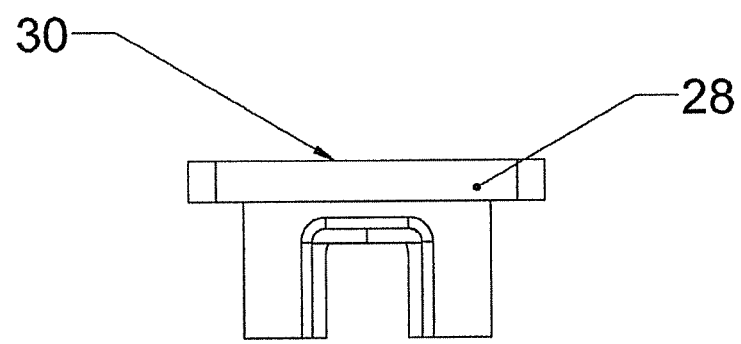
FIG. 28 is a side elevation view of an embodiment of the expandable horizontal wedge of the expandable interbody cage shown in FIG. 25.
Figure 29:
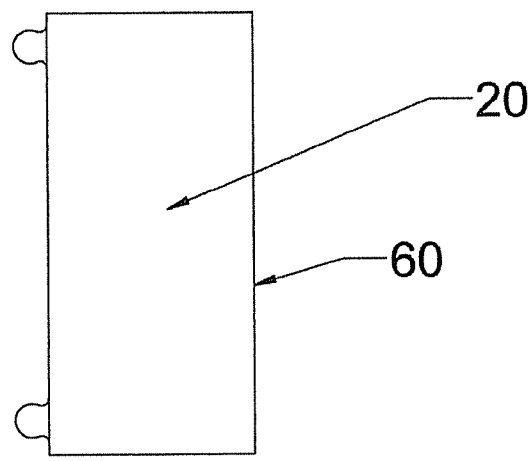
FIG. 29 is a top view of an embodiment of the leading end of the expandable interbody cage shown in FIG. 1.

Referring to FIGS. 15 and 16, the screw 25 of the preferred embodiment of the expandable interbody cage 10 is shown. The screw 25 is configured to prevent the vertical tapped sliding wedges 26, 27 from converging past the mid-way point on the screw 25, which those in the art will appreciate that this feature ensures that the horizontal slotted wedge 28 will expand at a uniform height. The screw 25 is a continuous component having threads disposed thereon.

Referring to FIGS. 17 through 24, enlarged fragmentary views of the vertical tapped sliding wedges 26, 27 are shown, illustrating the angular configuration of said wedges 26, 27 and the opening 24 of said wedges 26, 27 that permits the screw to thread there through, causing said wedges 26, 27 to converge towards each other.

Referring to FIGS. 25 through 28, enlarged fragmentary views of the rectangular-shaped horizontal slotted wedge 28 of the expandable interbody cage 10 are shown, which also serves as the top surface 30 of said cage 10. When attached to the expandable interbody cage 10, the horizontal slotted wedge 28 acts as a containment chamber for the biologics that are injected via penetrations 52 at the trailing end 50 of said cage 10. The horizontal slotted wedge 28 has risers 31, 32 that touch the bottom surface 40 of the expandable interbody cage 10 while it is in an unexpanded state or rises a distance above the bottom surface 40 when said cage 10 is in an expanded state. When said cage 10 is in an unexpanded state, risers 31 and 32 are simply at rest and flush with bottom surface 40, and are not connected or anchored to said bottom surface 40.

Referring to FIGS. 29 through 32, enlarged fragmentary views of the bullet nose 20 of the expandable interbody cage 10 are shown, which can be removed from said cage 10 as shown in FIGS. 13 and 14. One flat side of the bullet nose 20 serves as the leading end 20 of the expandable interbody cage 10, while one flat side 70 serves as the top angle of the bullet nose 20 and the other side 80 serves as the bottom angle of said bullet nose 20. It should be appreciated that the bullet shape of the leading end 20, as opposed to a flat shape, encourages ease of placement of the expandable interbody cage 10 in its desired position adjacent to vertebrae in the spine.

Although the present invention has been described in terms of preferred embodiments, other embodiments, including the number of parts, dimensions, and configurations will be apparent to those skilled in the art. All features disclosed in connection with any one embodiment can be readily adapted for use in other embodiments herein.

What is claimed is:

1. An expandable spinal fusion interbody cage comprising:
    a first portion and a second portion, wherein said first portion is substantially contained within said second portion;
    a leading end for insertion into the space between two adjacent vertebrae and a trailing end opposing said leading end;
    a top and bottom surface between said leading and trailing ends, generally parallel, each having openings thereon to promote biologics to permit bone growth;
    opposite sides between said top and bottom surfaces;
        a horizontal slotted wedge member having four support risers that are at rest and flush with said bottom surface of said cage when said cage is in an unexpanded state;
    two vertical tapped sliding wedges, each having a circular opening thereon that are threaded to accept a screw, which when actuated by said screw causes separation of said first portion and said second portion of said cage; and
    a screw that traverses the body of said cage with one end that penetrates into said leading end, the screw having a head that is visible from said trailing end;
    wherein when said first portion of said cage is actuated by rotating said screw and said vertical tapped sliding wedges converge towards each other, the overall height of said cage increases while the overall length of said cage remains constant; and
    wherein said to surface of said cage, when said cage is in a fully expanded state, forms a graduated angular relationship to auto-adjust UP to 12 degrees in an anterior-posterior direction to maintain and correct lordosis.

2. The cage of claim 1, wherein said openings on said top and bottom surfaces are generally 14 mm×6 mm.

3. The cage of claim 1, wherein said opposite sides are a flat solid surface.

4. The cage of claim 1, wherein said opposite sides have openings to promote biologics to permit bone growth.

5. The cage of claim 1, wherein said horizontal wedge member is in an angular relationship with said vertical tapped sliding wedges.

6. The cage of claim 1, wherein the vertical sliding tapped wedge located nearest said leading edge of said cage is reversed tapped to permit said wedge to converge towards the opposing vertical wedge as said screw is rotated.

7. The cage of claim 1, wherein said leading end has two angular surfaces and one vertical, flat surface such that said leading end is trapezoidal in shape.

8. The cage of claim 7, wherein said leading end is tapered for facilitating the insertion of said cage between two adjacent vertebral bodies.

9. The cage of claim 1, wherein said trailing end has four openings having a diameter in the range of 1 mm to 2 mm to permit the flow of biologics into said cage from an insertion/injection tool.

10. The cage of claim 1, wherein said trailing end has two openings having a diameter in the range of 2 mm to 4 mm that are configured to accept an insertion/injection tool to place said cage in its desired location adjacent to two vertebrae.

11. The cage of claim 1, wherein said cage can expand to a height in the range of 5 mm to 20 mm.

12. The cage of claim 1, having a plurality of openings capable of retaining biologics to promote the growth of bone.

13. The cage of claim 1, wherein said cage has a depth and width in the range of 10 mm to 20 mm for use in the cervical spine.

14. The cage of claim 1, wherein said cage has a depth and width in the range of 15 mm to 30 mm for use in the thoracic spine.

15. The cage of claim 1, wherein said cage has a depth in the range of 20 mm to 35 mm and a width in the range of 10 mm to 40 mm for use in the lumbar spine.

16. The cage of claim 1, wherein said separation of said first portion and said second portion of said cage occurs in a substantially orthogonal direction in regard to said screw.

17. The cage of claim 1, wherein said cage can be coupled with another expandable spinal interbody cage while in situ.

18. The cage of claim 1, wherein said biologics can be placed in said cage while said cage is in situ.

19. The cage of claim 1, wherein said cage is fabricated from plastic.

20. The cage of claim 1, wherein said cage is fabricated from human bone.

21. The cage of claim 1, wherein said cage is fabricated from PEEK.

* * * * *